United States Patent
Ogura et al.

(10) Patent No.: US 6,697,158 B2
(45) Date of Patent: Feb. 24, 2004

(54) MEASURING APPARATUS UTILIZING ATTENUATED TOTAL REFLECTION

(75) Inventors: Nobuhiko Ogura, Kaisei-machi (JP); Nobufumi Mori, Kaisei-machi (JP); Katsumi Hayashi, Kaisei-machi (JP); Toshihito Kimura, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 101 days.

(21) Appl. No.: 10/113,960

(22) Filed: Apr. 2, 2002

(65) Prior Publication Data

US 2002/0154312 A1 Oct. 24, 2002

(30) Foreign Application Priority Data

Apr. 3, 2001 (JP) ........................................ 2001-104695

(51) Int. Cl.[7] .............................................. G01N 21/55
(52) U.S. Cl. ........................ 356/445; 356/128; 356/136
(58) Field of Search ............................... 356/128, 445, 356/136

(56) References Cited

U.S. PATENT DOCUMENTS

| | | | |
|---|---|---|---|
| 5,875,032 A | * | 2/1999 | Naya .......................... 356/445 |
| 6,208,422 B1 | * | 3/2001 | Naya .......................... 356/445 |
| 6,340,448 B1 | * | 1/2002 | Naya et al. .................. 356/445 |
| 6,417,925 B1 | * | 7/2002 | Naya ........................... 356/128 |

FOREIGN PATENT DOCUMENTS

| | | |
|---|---|---|
| JP | 6-167443 | 6/1994 |
| JP | 11-326194 | 11/1999 |

OTHER PUBLICATIONS

Spectral Researches, vol. 47 No. 1 (1998, pp. 21 to 23 and pp. 26 to 27).

* cited by examiner

Primary Examiner—F. L. Evans
Assistant Examiner—Kara Geisel
(74) Attorney, Agent, or Firm—Sughrue Mion, PLLC (57) ABSTRACT

Disclosed herein is a measuring apparatus utilizing attenuated total reflection. The measuring apparatus is equipped with a dielectric block, a thin film layer formed on one surface of the dielectric block, an optical system for making a light beam enter the dielectric block so that a condition for total internal reflection is satisfied at an interface between the dielectric block and the thin film layer, and a two-piece photodiode for detecting the light beam totally reflected at the interface. When attenuated total reflection is detected a plurality of times for a single sample, the two-piece photodiode is disposed at a predetermined position relative to a dark line when a first measurement is made. The two-piece photodiode is also disposed at the same position as the predetermined position stored in a storage unit when a second measurement and measurements thereafter are made.

9 Claims, 5 Drawing Sheets

MEASURING APPARATUS UTILIZING ATTENUATED TOTAL REFLECTION

BACKGROUND OF THE INVENTION

1. Field of the Invention

The present invention relates to a measuring apparatus utilizing attenuated total reflection (hereinafter referred to as ATR), such as a surface plasmon resonance measuring apparatus for quantitatively analyzing a substance in a sample by utilizing excitation of surface plasmon, and more particularly to a measuring apparatus, utilizing ATR, of a type that detects a dark line occurring in a measuring light beam by ATR with the use of photodetection means consisting of light-receiving elements juxtaposed in a predetermined direction.

2. Description of the Related Art

In metals, if free electrons are caused to vibrate in a group, a compression wave called a plasma wave will be generated. The compression wave, generated in the metal surface and quantized, is called surface plasmon.

There have hitherto been proposed various kinds of surface plasmon resonance measuring apparatuses for quantitatively analyzing a substance in a sample by taking advantage of a phenomenon that surface plasmon is excited by a light wave. Among such apparatuses, one employing a system called "Kretschmann configuration" is particularly well known (e.g., see Japanese Unexamined Patent Publication No. 6(1994)-167443).

The surface plasmon resonance measuring apparatus employing the "Kretschmann configuration" is equipped with a dielectric block formed, for example, into the shape of a prism; a metal film, formed on one surface of the dielectric block, for placing a sample thereon; and a light source for emitting a light beam. The measuring apparatus is further equipped with an optical system for making the light beam enter the dielectric block so that a condition for total internal reflection (TIR) is satisfied at the interface between the dielectric block and the metal film and that ATR due to surface plasmon resonance can occur; and photodetection means for measuring the intensity of the light beam totally reflected at the interface, and thereby detecting surface plasmon resonance.

To obtain various angles of incidence in the aforementioned manner, a relatively thin light beam can be deflected so that it strikes the above-mentioned interface at different angles of incidence, or a relatively thick beam can be emitted convergently or divergently so that the components thereof strike the interface at various angles of incidence. In the former, the light beam whose reflection angle varies with the deflection thereof can be detected by a small photodetector that is moved in synchronization with the light beam deflection, or by an area sensor extending along a direction where the reflection angle varies. In the latter, on the other hand, the light beams reflected at various angles can be detected by an area measuring apparatus extending in a direction where all the reflected light beams are received.

In the surface plasmon resonance measuring apparatus mentioned above, an evanescent wave having electric field distribution is generated in a sample in contact with the metal film, if a light beam strikes the metal film at a specific incidence angle $\theta_{sp}$ greater than a critical incidence angle at which total internal reflection (TIR) takes place. The generated evanescent wave excites surface plasmon at the interface between the metal film and the sample. When the wave vector of the evanescent wave is equal to the wave number of the surface plasmon and therefore the wave numbers between the two are matched, the evanescent wave resonates with the surface plasmon and the light energy is transferred to the surface plasmon, whereby the intensity of the light satisfying TIR at the interface between the dielectric block and the metal film drops sharply. This sharp intensity drop is generally detected as a dark line by the above-mentioned photodetection means.

Note that the above-mentioned resonance occurs only when an incident light beam is a p-polarized light beam. Therefore, in order to make the resonance occur, it is necessary that a light beam be p-polarized before it strikes the interface.

If the wave number of the surface plasmon is found from the specific incidence angle $\theta_{sp}$ at which ATR takes place, the dielectric constant of a sample to be analyzed can be calculated by the following Equation:

$$K_{sp}(\omega)=(\omega/c)\{\in_m(\omega) \in_s\}^{1/2}/\{\in_m(\omega)+\in_s\}^{1/2}$$

where $K_{sp}$ represents the wave number of the surface plasmon, $\omega$ represents the angular frequency of the surface plasmon, c represents the speed of light in vacuum, and $\in_m$ and $\in_s$ represent the dielectric constants of the metal and the sample, respectively.

If the dielectric constant $\in_s$ of a sample is found, the density of a specific substance in the sample is found based on a predetermined calibration curve, etc. As a result, the dielectric constant of the sample, i.e., the properties of the sample related to the refractive index thereof can be quantitatively analyzed by finding the specific incidence angle $\theta_{sp}$ at which the intensity of the reflected light at the interface drops sharply.

In this kind of surface plasmon resonance sensor, photodetection means in the form of an array can be employed with the object of measuring the aforementioned incidence angle $\theta_{sp}$ with a high degree of accuracy and in a large dynamic range, as disclosed in Japanese Unexamined Patent Publication No. 11(1999)-326194. The photodetection means is constructed of a plurality of light-receiving elements juxtaposed in a predetermined direction. The light-receiving elements are disposed to respectively receive the components of a light beam reflected at the aforementioned interface at various angles of reflection.

In that case, differentiation means is provided to differentiate the photodetection signals output by the light-receiving elements of the aforementioned photodetection means, in the direction where the light-receiving elements are juxtaposed. The properties of the sample related to the refractive index thereof are often analyzed based on differentiated values output by the differentiation means, particularly the differentiated value corresponding to a dark line that occurs in a reflected light beam. The differentiation means can employ, for example, means for detecting the difference between the outputs of two adjacent light-receiving elements.

In the case of detecting the properties of a sample corresponding to the aforementioned incidence angle $\theta_{sp}$ by obtaining the difference between the outputs of two adjacent light-receiving elements, it is possible to employ a two-piece photodiode instead of the array-shaped photodetection means, if a large dynamic range is not required. In that case, the difference between the outputs of two photodiodes corresponds to the position of the aforementioned dark line in the direction where the photodiodes are arranged. Based on the difference, the properties of a sample corresponding to the aforementioned incidence angle $\theta_{sp}$ can be detected.

On the other hand, as a similar resonance measuring apparatus making use of ATR, there is known a leaky mode sensor (e.g., see "Spectral Researches," Vol. 47, No.1 (1998), pp. 21 to 23 and pp. 26 to 27). This leaky mode measuring apparatus is equipped with a dielectric block formed, for example, into the shape of a prism; a cladding layer formed on one surface of the dielectric block; and an optical waveguide layer, formed on the cladding layer, for placing a sample thereon. The leaky mode sensor is further equipped with a light source for emitting a light beam; an optical system for making the light beam enter the dielectric block at various angles of incidence so that a condition for total internal reflection (TIR) is satisfied at the interface between the dielectric block and the cladding layer and so that ATR occurs by a waveguide mode excited in the optical waveguide layer; and photodetection means for measuring the intensity of the light beam totally reflected at the interface between the dielectric block and the cladding layer, and thereby detecting the excited state of the waveguide mode, that is, ATR.

In the leaky mode measuring apparatus mentioned above, if a light beam strikes the cladding layer through the dielectric block at incidence angles greater than a critical incidence angle at which TIR takes place, the light beam is transmitted through the cladding layer and then only light with a specific wave number, incident at a specific incidence angle, propagates through the optical waveguide layer in a waveguide mode. If the waveguide mode is excited in this manner, the greater part of the incident light is confined within the optical waveguide layer, and consequently, ATR occurs in which the intensity of light totally reflected at the above-mentioned interface drops sharply. Since the wave number of the light propagating through the optical waveguide layer depends on the refractive index of a sample on the optical waveguide layer, both the refractive index of the sample and the properties of the sample related to the refractive index thereof can be analyzed by finding the above-mentioned specific incidence angle $\theta_{sp}$ at which ATR takes place.

The leaky mode measuring apparatus can also employ the aforementioned array-shaped photodetection means or two-piece photodiode, because the apparatus detects the position of a dark line which occurs in a reflected light beam by ATR.

However, in the case where the aforementioned array-shaped photodetection means is employed in a measuring apparatus utilizing ATR, such as the aforementioned surface plasmon resonance measuring apparatus and leaky mode measuring apparatus, there is a problem that accuracy of measurement will be reduced.

SUMMARY OF THE INVENTION

The present invention has been made in view of the circumstances mentioned above. Accordingly, it is the primary object of the present invention to provide a measuring apparatus, utilizing ATR, which is capable of assuring high accuracy of measurement.

To achieve this end and in accordance with the present invention, there is provided a first measuring apparatus utilizing attenuated total reflection, comprising:
a dielectric block;
a thin film layer, formed on one surface of the dielectric block, for placing a sample thereon;
a light source for emitting a light beam;
an optical system for making the light beam enter the dielectric block at various angles of incidence so that a condition for total internal reflection is satisfied at an interface between the dielectric block and the thin film layer;
photodetection means, comprising a plurality of light-receiving elements juxtaposed in a predetermined direction and disposed to respectively receive components of the light beam totally reflected at the interface, for detecting attenuated total reflection from a dark line occurring in the totally reflected light beam;
movement means for moving the photodetection means in the direction where the plurality of light-receiving elements are juxtaposed;
position detection means for detecting position of the photodetection means moved by the movement means;
storage means for storing the position of the photodetection means detected by the position detection means; and
control means for controlling the movement means when the attenuated total reflection is detected a plurality of times for a single sample, and then disposing the photodetection means at a predetermined position relative to the dark line when a first measurement is made and also disposing the photodetection means at the same position as the predetermined position stored in the storage means when a second measurement and measurements thereafter are made.

In accordance with the present invention, there is provided a second measuring apparatus utilizing attenuated total reflection, comprising:
a dielectric block;
a metal film, formed on one surface of the dielectric block, for placing a sample thereon;
a light source for emitting a light beam;
an optical system for making the light beam enter the dielectric block at various angles of incidence so that a condition for total internal reflection is satisfied at an interface between the dielectric block and the metal film;
photodetection means, comprising a plurality of light-receiving elements juxtaposed in a predetermined direction and disposed to respectively receive components of the light beam totally reflected at the interface, for detecting attenuated total reflection due to surface plasmon resonance from a dark line occurring in the totally reflected light beam;
movement means for moving the photodetection means in the direction where the plurality of light-receiving elements are juxtaposed;
position detection means for detecting position of the photodetection means moved by the movement means;
storage means for storing the position of the photodetection means detected by the position detection means; and
control means for controlling the movement means when the attenuated total reflection is detected a plurality of times for a single sample, and then disposing the photodetection means at a predetermined position relative to the dark line when a first measurement is made and also disposing the photodetection means at the same position as the predetermined position stored in the storage means when a second measurement and measurements thereafter are made.

In accordance with the present invention, there is provided a third measuring apparatus utilizing attenuated total reflection, comprising:
a dielectric block;

a cladding layer formed on one surface of the dielectric block;

an optical waveguide layer, formed on the cladding layer, for placing a sample thereon;

a light source for emitting a light beam;

an optical system for making the light beam enter the dielectric block at various angles of incidence so that a condition for total internal reflection is satisfied at an interface between the dielectric block and the cladding layer;

photodetection means, comprising a plurality of light-receiving elements juxtaposed in a predetermined direction and disposed to respectively receive components of the light beam totally reflected at the interface, for detecting attenuated total reflection due to a waveguide mode excited in the optical waveguide layer, from a dark line occurring in the totally reflected light beam;

movement means for moving the photodetection means in the direction where the plurality of light-receiving elements are juxtaposed;

position detection means for detecting position of the photodetection means moved by the movement means;

storage means for storing the position of the photodetection means detected by the position detection means; and control means for controlling the movement means when the attenuated total reflection is detected a plurality of times for a single sample, and then disposing the photodetection means at a predetermined position relative to the dark line when a first measurement is made and also disposing the photodetection means at the same position as the predetermined position stored in the storage means when a second measurement and measurements thereafter are made.

In the three measuring apparatuses, the photodetection means may be constructed of a two-piece photodiode or photodiode array.

The inventors have made various investigations and experiments with respect to a mechanism causing a reduction in accuracy of measurement when employing array-shaped photodetection means in the conventional measuring apparatus utilizing ATR, and found that the reduction in accuracy of measurement results from a difference in physical characteristics among a plurality of light-receiving elements constituting the photodetection means.

That is, since the aforementioned specific incidence angle (at which ATR occurs) varies from sample to sample, a light-receiving element of a plurality of light-receiving elements which detects a dark line also varies with a sample. In surface plasmon resonance measuring apparatuses and leaky mode measuring apparatuses, the properties of a sample are analyzed by detecting the position of the light-receiving element detecting the dark line. Therefore, if there is a difference in physical characteristics among a plurality of light-receiving elements, the difference will have influence on the detection of the dark line and reduce accuracy of measurement.

In view of the above-mentioned facts, the measuring apparatus of the present invention is provided with movement means for moving photodetection means in the direction where a plurality of light-receiving elements are juxtaposed, position detection means for detecting position of the photodetection means moved by the movement means, and storage means for storing the position of the photodetection means detected by the position detection means. The measuring apparatus is further provided with control means for controlling the movement means when the attenuated total reflection is to be detected a plurality of times for a single sample. The photodetection means is disposed at a predetermined position relative to the dark line when a first measurement is made, and also the photodetection means is disposed at the same position as the predetermined position stored in the storage means when a second measurement and measurements thereafter are made.

With this arrangement, the relative position of the photodetection means with respect to the dark line position can be maintained constant without depending on the aforementioned specific incidence angle $\theta_{sp}$, i.e., a sample. In this state, a plurality of measurements can be started. Therefore, even when there is a difference in physical characteristics among a plurality of light-receiving elements constituting array-shaped photodetection means, the influence of the difference in physical characteristics on the detection of the dark line position becomes constant for each measurement and therefore there is no possibility that accuracy of measurement will be reduced due to the difference in physical characteristics.

BRIEF DESCRIPTION OF THE DRAWINGS

The present invention will be described in further detail with reference to the accompanying drawings wherein.

DESCRIPTION OF THE PREFERRED EMBODIMENTS

Figure 1:
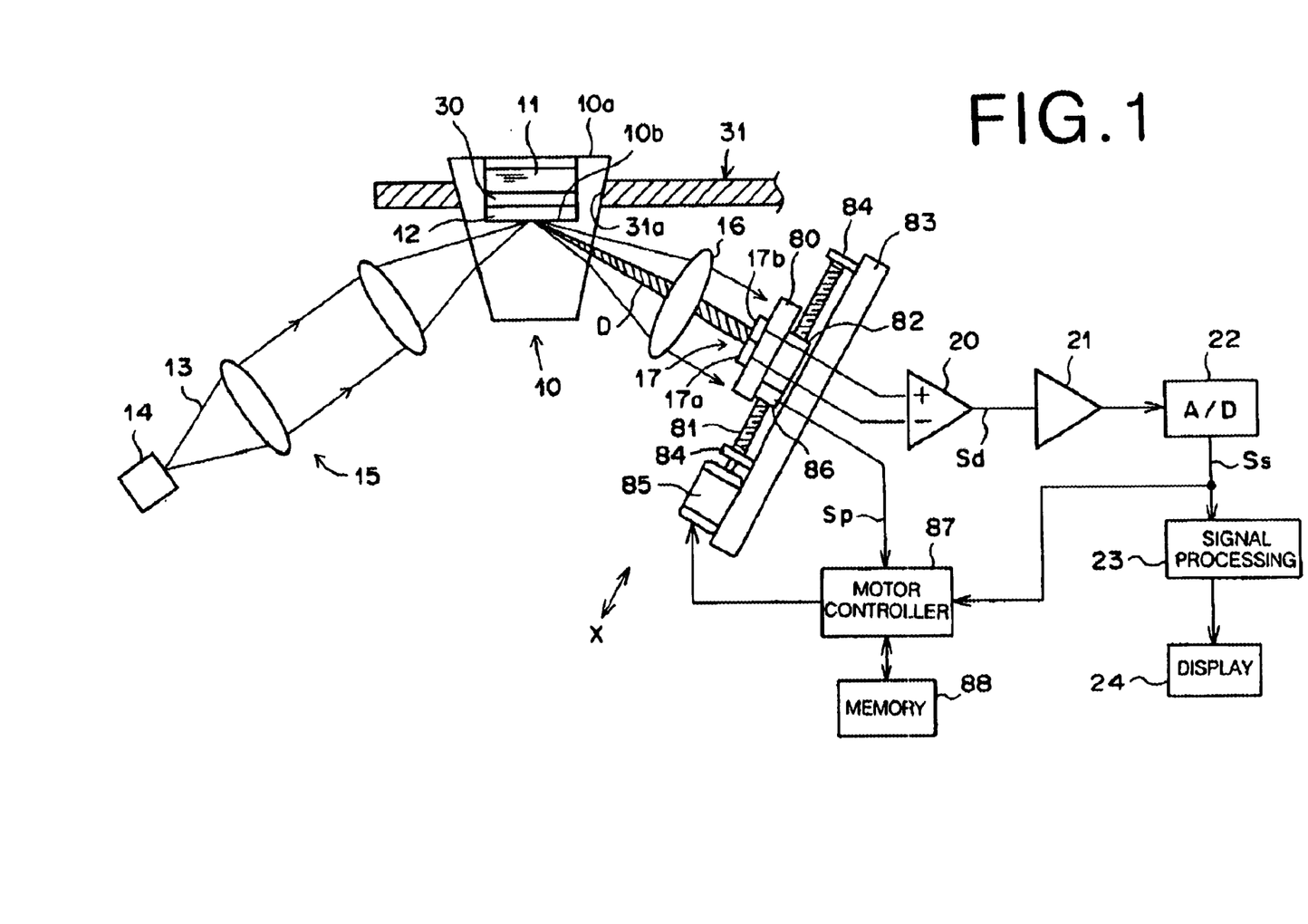
FIG. 1 is a side view showing a surface plasmon resonance measuring apparatus constructed according to a first embodiment of the present invention.

Referring now in greater detail to the drawings and initially to FIG. 1, there is shown a surface plasmon resonance measuring apparatus in accordance with a first embodiment of the present invention. The surface plasmon resonance measuring apparatus has a dielectric block 10 and a metal film 12. The dielectric block 10 is formed, for example, into a truncated substantially quadrangular pyramid shape. The metal film 12 is formed on one surface (top surface in FIG. 1) of the dielectric block 10, and is made, for example, of gold, silver, copper, aluminum, etc.

The dielectric block 10 is formed, for example, from transparent resin, etc., and is thickened at a portion 10a thereof to form a sample holding portion in which a liquid sample 11 is stored. In the first embodiment, a sensing medium 30 (which is to be described later) is fixed on the metal film 12.

The dielectric block 10 and the metal film 12 constitute a disposable measuring chip. A plurality of disposable measuring chips are fitted in chip holding holes 31a formed in a turntable 31, respectively. With the dielectric blocks 10 thus fitted in the chip holding holes 31a of the turntable 31, the turntable 31 is intermittently rotated at intervals of a predetermined angle. If a dielectric block 10 is stopped at a predetermined position, the liquid sample 11 is dropped into the dielectric block 10 and held within the sample holding portion 10a. If the turntable 31 is further rotated through the predetermined angle, the dielectric block 10 is moved to the measuring position shown in FIG. 1 and is stopped there.

The surface plasmon resonance measuring apparatus of the first embodiment, in addition to the dielectric block 10, has a laser light source 14, an optical system 15, and a collimator lens 16. The light source 14 is constructed of a semiconductor laser, etc., and is used for emitting a single light beam 13. The optical system 15 is used for making the light beam 13 enter the dielectric block 10 so that various angles of incidence are obtained with respect to an interface 10b between the dielectric block 10 and the metal film 12. The collimator lens 16 is used for collimating the light beam 13 totally reflected at the interface 10b.

The surface plasmon resonance measuring apparatus is further equipped with a two-piece photodiode 17, a first differential amplifier 20 connected to the two-piece photodiode 17, a second amplifier 21, an A/D converter 22, a signal processing section 23, and display means 24 connected to the signal processing section 23. The two-piece photo diode 17 is used as photodetection means for detecting the collimated light beam 13. The second amplifier 21 is used for amplifying the output of the differential amplifier 20. The A/D converter 22 is used for converting the output of the second amplifier 21 into a digital signal. The signal processing section 23 consists of a computer system for detecting the properties of the sample 11, based on an output signal $S_s$ from the A/D converter 22.

The two-piece photodiode 17 consists of two photodiodes 17a, 17b juxtaposed in the direction of arrow X shown in FIG. 1. Therefore, the incidence position of the light beam 13 totally reflected at the interface 10b with respect to the two-piece photodiode 17 will change in the direction where the two photodiodes 17a, 17b are arranged, if the reflection angle changes.

The two-piece photodiode 17 is mounted on a movable table 80, which is in turn mounted on a threaded block 82. The threaded block 82 meshes with a fine screw 81 extending in the direction of arrow X. The movable table 80 is supported by guide means (not shown) so that it is free to move in the direction parallel to the axial direction of the fine screw 81. Both ends of the fine screw 81 are rotatably supported by two support members 84, 84 mounted on a stationary table 83. One end of the fine screw 81 is connected to the driving shaft of a stepping motor 85 which rotates in positive and reverse directions. Therefore, if the fine screw 81 is rotated by the stepping motor 85, the threaded block 82 is moved in the direction of arrow X, and the two-piece photodiode 17 mounted on the movable table 80 is linearly moved in that direction. In the first embodiment, the above-mentioned components 80 to 85 constitute means for moving the two-piece photodiode 17.

The position in the direction of arrow X of the movable table 80, i.e., the two-piece photodiode 17 is detected by an encoder (position detection means) 86. An output signal $S_p$ of the encoder 86 representing the detected position is input to a motor controller 87. This motor controller 87 is used for controlling the stepping motor 85 and receives the aforementioned output $S_s$ from the A/D converter 22. The motor controller 87 is also connected to memory 88 for storing position of the two-piece photodiode 17.

A description will hereinafter be given of how a sample is analyzed by the surface plasmon resonance measuring apparatus constructed as described above. In the first embodiment, as described previously, a plurality of dielectric blocks 10 are fitted in the turntable 31, the turntable 31 is rotated intermittently at intervals of a predetermined angle, and the dielectric blocks 10 are disposed one by one at a predetermined measuring position where the light beam 13 is irradiated to the dielectric block 10, as shown in FIG. 1. In addition, in the first embodiment, to examine the bond between the sensing substance 30, fixed on the metal film 12 of the dielectric block 10, and a specific substance in the liquid sample 11, each dielectric block 10 is disposed at the measuring position a plurality of times and is measured.

The light beam 13 emitted divergently from the laser light source 14 converges on the interface 10b between the dielectric block 10 and the metal film 12 by operation of the optical system 15. Therefore, the light beam 13 includes components incident at various incidence angles θ with respect to the interface 10b. Note that the incidence angles θ are greater than a critical incidence angle at which total internal reflection takes place. Hence, the light beam 13 is totally reflected at the interface 10b, and the reflected light beam 13 includes components reflected at various angles.

Note that the light beam 13 is made to strike the interface 10b as a p-polarized light beam. For this reason, the laser light source 14 needs to be disposed so that the polarization direction thereof becomes a predetermined direction. Alternatively, the polarization direction of the light beam 13 may be controlled with a wavelength plate, a polarizing plate, etc.

Figure 2A:
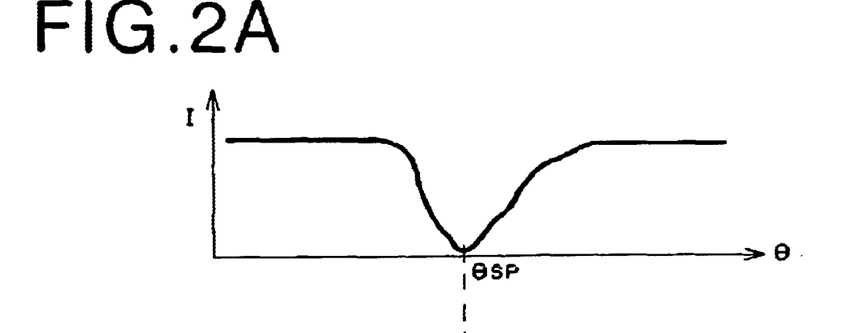
FIG. 2A is a diagram used to explain the relationship between the incidence angle of a light beam and the intensity of the light beam totally reflected at an interface.
Figure 2B:
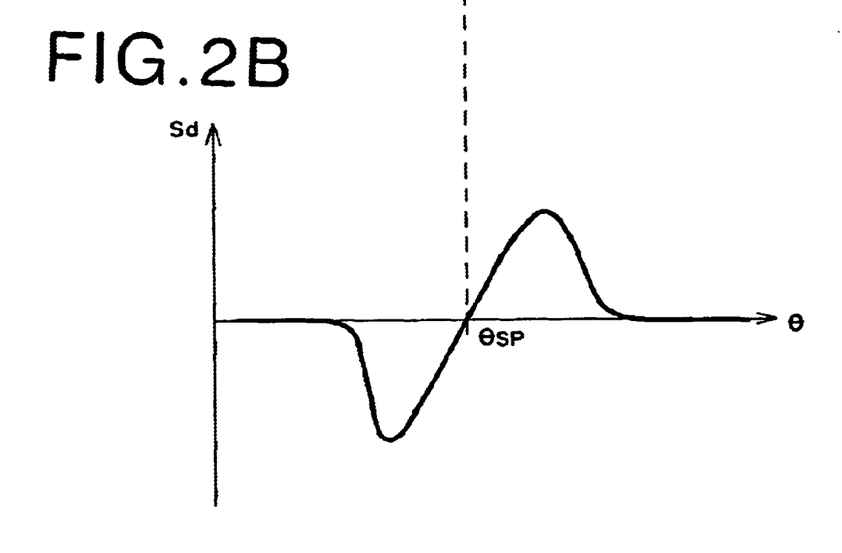
FIG. 2B is a diagram used to explain the relationship between the incidence angle of the light beam and the output of a differential amplifier connected to a two-piece photodiode.

The light beam 13 satisfying total internal reflection at the interface 10b is collimated by the collimator lens 16 and is detected by the two-piece photodiode 17. FIG. 2A shows the relationship between the incidence angle θ of the light beam 13 and the intensity of the light beam 13 totally reflected at the interface 11b. FIG. 2B shows the relationship between the incidence angle θ of the light beam 13 and the output $S_d$ of the differential amplifier 20 connected to the two-piece photodiode 17.

Suppose that the relationship between the incidence angle θ of the light beam 13 and the intensity of the light beam 13 totally reflected at the interface 11b becomes like that shown in FIG. 2A. The light, incident at a specific angle $\theta_{sp}$ on the interface 10b between the metal film 12 and the sample 11, excites a surface plasmon on the interface 10b. Because of this, for the light incident at the specific angle $\theta_{sp}$, the intensity I of the reflected light drops sharply. That is, the specific incidence angle $\theta_{sp}$ is an incidence angle at which ATR occurs. The intensity I of the reflected light becomes the minimum value at the specific incidence angle $\theta_{sp}$. This sharp drop in the intensity I of the reflected light is observed as a dark line in the reflected light, as shown at D in FIG. 1.

When a first measurement of the liquid sample 11 in each dielectric block 10 is made, the stepping motor 85 is driven by the motor controller 87 and the movable table 80 is moved from its lowest position to its highest position. Note that the moving range of the movable table 80, i.e., the moving range of the two-piece photodiode 17 is within a range in which the light beam 13 can be irradiated to the two-piece photodiode 17.

When the two-piece photodiode 17 is moved in this manner, the output $S_d$ of the differential amplifier 20 changes as shown in FIG. 2B. Note that the horizontal axis in FIG. 2B represents the position of the two-piece photodiode 17. To cause FIG. 2B to correspond to FIG. 2A, the position is represented by the incidence angle θ of the light beam 13, which strikes the center position of the two-piece photodiode 17 corresponding to the gap between the two photodiodes 17a and 17b, with respect to the interface 10b.

As shown in FIG. 2B, the output $S_d$ of the differential amplifier 20 becomes zero when the movable table 80 is at the lowest position (corresponding to a position at which the incidence angle θ is minimum), because the quantities of the light beams incident on the two photodiodes 17a and 17b are equal to each other. If the movable table 80 is moved upward from the lowest position and the upper photodiode 17b reaches the aforementioned dark line D, the output $S_d$ of the differential amplifier 20 becomes a negative value. If the movable table 80 is further moved and the lower photodiode 17a reaches the dark line D, the output $S_d$ of the differential amplifier 20 is increased. When the center of the dark line D is aligned with the gap between the photodiodes 17a and 17b, the output $S_d$ of the differential amplifier 20 becomes zero again. Next, if the movable table 80 is further moved upward and the portion of the dark line D in the upper photodiode 17b is gradually reduced, the output $S_d$ of the differential amplifier 20 becomes a positive value. If the portion of the dark line D in the lower photodiode 17a is reduced, the output $S_d$ of the differential amplifier 20 is reduced. When the movable table 80 is further moved upward and the dark line D is outside the photodiodes 17a and 17b, the output $S_d$ of the differential amplifier 20 becomes zero again.

Note that the foregoing description is based on the assumption that there is no difference in physical characteristics between the two photodiodes 17a, 17b. The case where there is a difference in physical characteristics will be described in detail later.

The output $S_d$ of the differential amplifier 20 is amplified by the amplifier 21 and is converted into a digital signal by the A/D converter 22. During the time the movable table 80 is moved, the output $S_s$ of the A/D converter 22 is input to the motor controller 87. When the output $S_s$ of the A/D converter 22 becomes zero for the second time, that is, when the dark line D is aligned with the gap between the photodiodes 17a and 17b, the motor controller 87 holds the output signal $S_p$ of the encoder 85 representing the position of the movable table 80. The output signal $S_d$ is caused to correspond with the dielectric block 10 being measured (more specifically, it is caused to correspond with the identification number of the chip holding hole 31 of the turntable 31 in which the dielectric block 10 being measured is fitted), and is stored in the memory 88.

Thereafter, if the output $S_s$ of the A/D converter 22 does not become zero (third zero), the motor controller 87 judges the measurement of the liquid sample 11 of the dielectric block 10 to be unsuccessful, and the stored signal $S_p$ is deleted from the memory 88.

The output $S_s$ of the A/D converter 22 is also input to the signal processing section 23. If the signal processing section 23 confirms that the output $S_s$ has become zero three times, the signal processing section 23 judges the measurement of the liquid sample 11 of the dielectric block 10 to be successful. The value of zero is displayed on the display means 24 as a first measured value.

When a first measurement is performed on a plurality of dielectric blocks 10 on the turntable 31, the aforementioned operation is carried out for each of the dielectric blocks 10.

When a second measurement and measurements thereafter are performed on one dielectric block 10, the motor controller 87 reads out the signal $S_p$, stored in the memory 88, which corresponds to the dielectric block 10. The motor controller 87 drives the stepping motor 85, based on the signal output $S_s$, and moves the movable table 80 to the position represented by the signal $S_p$. If the movable table 80 is positioned in this manner, the dielectric block 10 being subjected to a second measurement and measurements thereafter is disposed at the same position as the position where the center of the dark line D was received by the gap between the photodiodes 17a and 17b at the time of the first measurement.

When a second measurement and measurements thereafter are performed on the sample 11 of each dielectric block 10, the output $S_s$ of the A/D converter 22 is input to the signal processing section 23, with the two-piece photodiode 17 disposed at the above-mentioned position for each dielectric block 10.

If the dielectric constant (i.e., refractive index) of a substance in contact with the metal film 12 (see FIG. 1) of the dielectric block 10 changes and therefore the curve shown in FIG. 2A is horizontally shifted, the output $S_d$ of the differential amplifier 20 shown in FIG. 2A (i.e., the output $S_s$ of the A/D converter 22) is vertically shifted according to the horizontal shift. If there is such a change when a second measurement and measurements thereafter are made, the output $S_s$ of the A/D converter 22 will not become zero, even if the two-piece photodiode 17 is disposed at the same position as that in the first measurement. Therefore, if the output $S_s$ of the A/D converter 22 is continuously detected with the lapse of time, a change in the refractive index of the substance in contact with the metal film 12, that is, a change in the properties of the substance can be detected.

In the first embodiment, the sensing medium 30 which bonds to a specific substance in the liquid sample 11 is fixed to the metal film 12, and according to the bonded state, the refractive index of the sensing medium 30 changes. Therefore, by continuously measuring the output Ss of the A/D converter 22, how the bonded state changes can be detected. In this case, both the liquid sample 11 and the sensing substance are samples to be analyzed. As an example of a combination of the specific substance and the sensing substance 30, there is combination of an antigen and an antibody.

In the first embodiment, when each dielectric block 10 is measured, the center of the dark line D is always aligned with the gap between the photodiodes 17a and 17b at the time of a first measurement, and then a plurality of measurements are started. Therefore, the problem of a reduction in accuracy of measurement resulting from a difference in physical characteristics between the light-receiving elements, which occurs in the aforementioned conventional apparatus employing array-shaped photodetection means, will not arise. As a result, accurate measurement becomes possible.

In addition, in the case where there is a difference in physical characteristics between the two photodiodes 17a and 17b, a plurality of measurements are started with the center of the dark line D shifted slightly from the gap between the photodiodes 17a and 17b, if the aforementioned operation is performed. However, since the shifted state is the same when each dielectric block 10 is measured, there is no possibility that accuracy of measurement will be reduced due to the difference in physical characteristic between the two photodiodes 17a and 17b.

In the first embodiment mentioned above, the dielectric block 10 and the metal film 12 constitute a disposable-measuring chip. However, even in the case where the dielectric blocks 10 are incorporated into the surface plasmon resonance measuring apparatus, the present invention can be applied, and the same effect can be obtained.

Figure 3:
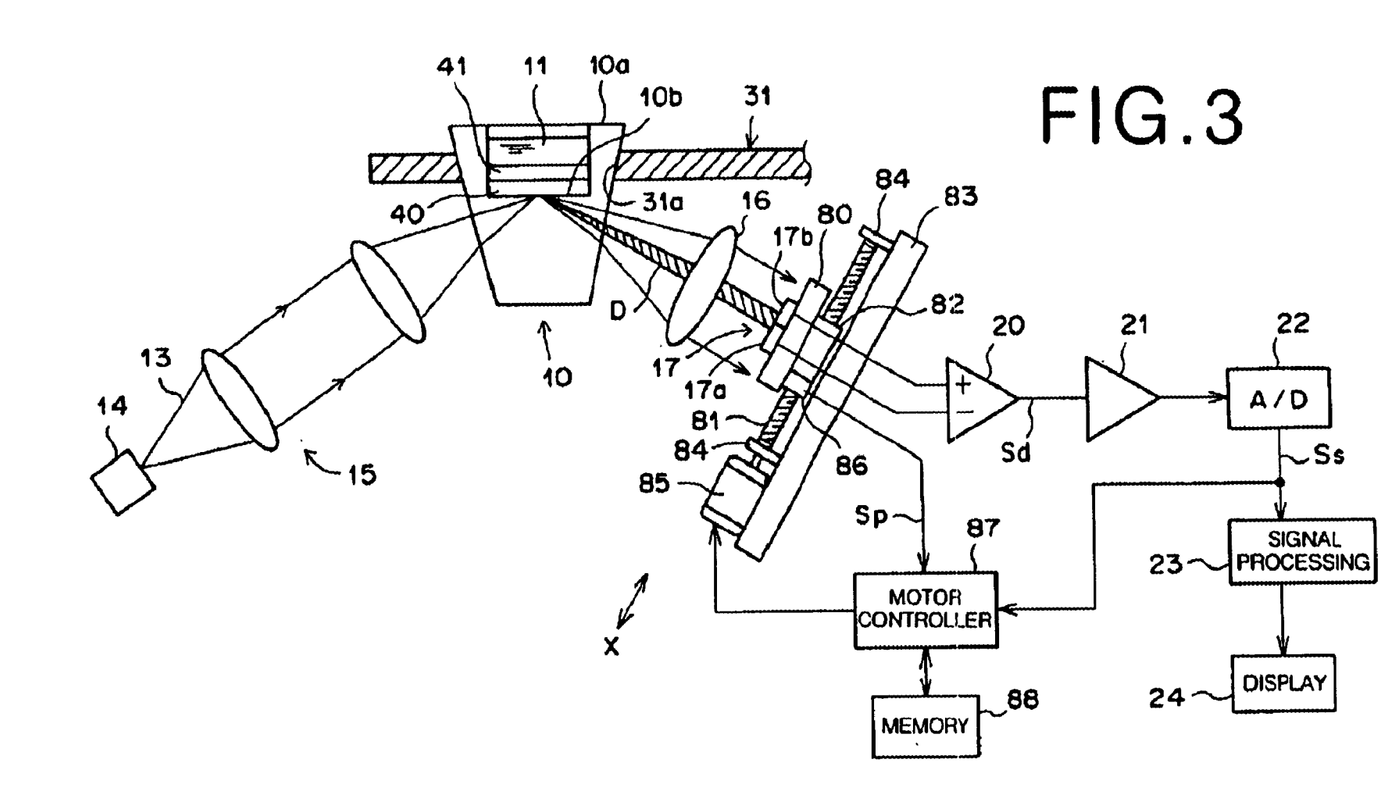
FIG. 3 is a side view showing a leaky mode measuring apparatus constructed according to a second embodiment of the present invention.

FIG. 3 shows a leaky mode measuring apparatus utilizing ATR, constructed according to a second embodiment of the present invention. Note in the figure that the same reference numerals are applied to the same parts as those in FIG. 1, and that a description thereof will not be given unless particularly necessary (the same applies to the following descriptions).

As with the first embodiment, the second embodiment is constructed so that it employs a plurality of dielectric blocks 10 as the measuring chips. Each dielectric block 10 has a cladding layer 40 formed on one surface thereof (e.g., the top surface in FIG. 11). The cladding layer 40 has an optical waveguide layer 41 formed thereon.

The dielectric block 10 is formed, for example, from synthetic resin, or optical glass such as BK7, etc. The cladding layer 40 is formed into the shape of a thin film by employing a dielectric lower in refractive index than the dielectric block 10, or metal such as gold, etc. The optical waveguide layer 41 is also formed into the shape of a thin film by employing a dielectric higher in refractive index than the cladding layer 40, such as polymethylmethacrylate (PMMA). The cladding layer 40 is 36.5 nm in thickness when it is formed from a thin gold film. The optical waveguide layer 41 is about 700 nm in thickness when it is formed from PMMA.

In the leaky mode measuring apparatus of the second embodiment, if a light beam 13 emitted from a laser light source 14 strikes the cladding layer 40 through the dielectric block 10 at incidence angles greater than an incidence angle at which total internal reflection (TIR) takes place, the light beam 13 is totally reflected at an interface 10b between the dielectric block 10 and the cladding layer 40. However, the light with a specific wave number, incident on the optical waveguide layer 41 through the cladding layer 40 at a specific incidence angle, propagates through the optical waveguide layer 41 in a waveguide mode. If the waveguide mode is thus excited, the greater part of the incident light is confined within the optical waveguide layer 41, and consequently, ATR occurs in which the intensity of the light totally reflected at the interface 10b drops sharply.

The wave number of the light propagating through the optical waveguide layer 41 depends on the refractive index of a sample 30 on the optical waveguide layer 41. Therefore, by detecting the aforementioned specific incidence angle at which ATR occurs, the refractive index of the sample 11 and the properties of the sample 11 related to the refractive index can be analyzed.

In the second embodiment, as with the first embodiment, the dark line D due to ATR is detected by a two-piece photodiode 17. In addition, the movement of the two-piece photodiode 17 and the control of the moved position are performed in the same manner as that in the first embodiment. Thus, the second embodiment is capable of obtaining the same effect as that in the first embodiment.

While the aforementioned two embodiments employ the two-piece photodiode 17 as the aforementioned photodetection means, the present invention can also employ array-shaped photodetection means, such as a photodiode array, etc., as the photodetection means. The array-shaped photodetection means is suitable in the case where the profile of intensity I such as that shown in FIG. 2A is detected and the aforementioned specific incidence angle $\theta_{sp}$ and a change in the angle are predicted from the profile.

In the case of employing the array-shaped photodetection means, the relative position of the photodetection means with respect to the dark line position is maintained constant without depending on the aforementioned specific incidence angle $\theta_{sp}$, i.e., a sample, if the movement and position control of the photodetection means are performed in the same manner as that in the first or second embodiment. In this state, a plurality of measurements can be started. Therefore, even when there is a difference in physical characteristics among a plurality of light-receiving elements constituting array-shaped photodetection means, the influence of the difference in physical characteristics on the detection of the dark line position becomes constant for each measurement and therefore there is no possibility that accuracy of measurement will be reduced due to the difference in physical characteristics.

Figure 4:
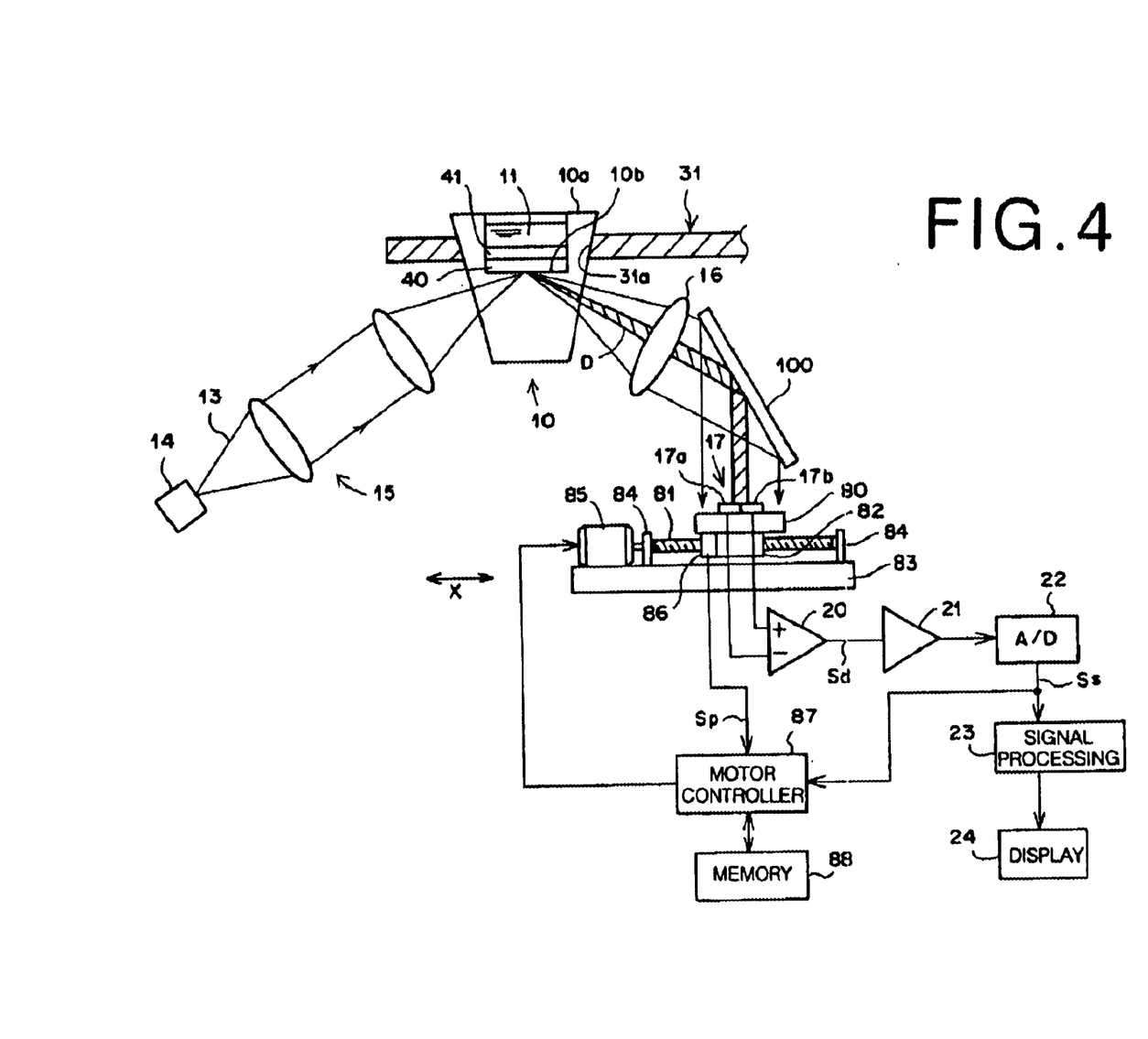
FIG. 4 is a side view showing a leaky mode measuring apparatus constructed according to a third embodiment of the present invention.

FIG. 4 shows a leaky mode measuring apparatus constructed according to a third embodiment of the present invention. The leaky mode measuring apparatus of the third embodiment basically differs from that of FIG. 3 in that it is provided with a mirror 100. The mirror 100 is used for reflecting a light beam 13, totally reflected at an interface 10b between a dielectric block 10 and a cladding layer 40, in a downward direction. In addition, a photodetection system is arranged according to the mirror 100.

That is, in the third embodiment, the light-receiving surface of a two-piece photodiode 17 is horizontally arranged and the two-piece photodiode 17 is constructed so that it is moved parallel to the interface 10b between the dielectric block 10 and the cladding layer 40 by a movable table 80.

In such a construction, the vibration due to the two-piece photodiode 17 being moved by the movable table 80 will occur principally in the moving direction, that is, the direction of arrow X. The direction of the vibration is parallel to the interface 10b. This prevents the position of the dark line D from greatly fluctuating due to vibration, and consequently, a reduction in accuracy of measurement is prevented. On the other hand, in the case where vibration is exerted in the direction perpendicular or nearly perpendicular to the interface 10, the position of the dark line D fluctuates greatly and therefore the problem of a reduction in accuracy of measurement is liable to occur.

Figure 5:
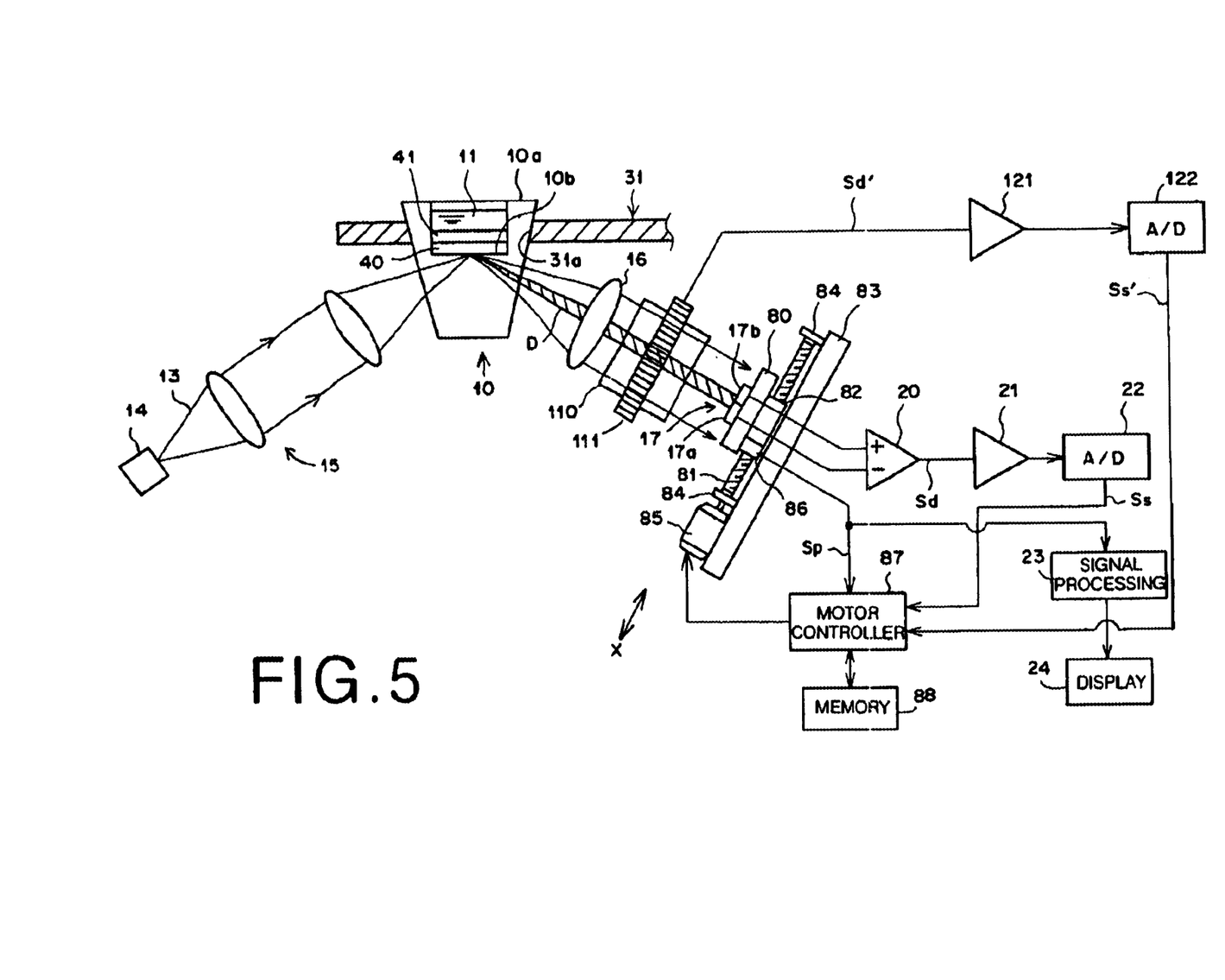
FIG. 5 is a side view showing a leaky mode measuring apparatus constructed according to a fourth embodiment of the present invention.

The construction in which the moving direction of the two-piece photodiode 17 is set as described above is also applicable to the surface plasmon resonance measuring apparatus shown in FIG. 1 and the leaky mode measuring apparatus of FIG. 3, and to the apparatus of FIG. 5 to be described later. Similarly, a reduction in accuracy of measurement due to vibration can be prevented.

FIG. 4 shows a leaky mode measuring apparatus constructed according to a fourth embodiment of the present invention. The leaky mode measuring apparatus of the fourth embodiment basically differs from that of FIG. 3 in that it is provided with abeam splitter 110, a line sensor 111, an amplifier 121, and an A/D converter 122. The beam splitter 110 is used for branching part of a light beam 13, totally reflected at an interface 10b between a dielectric block 10 and a cladding layer, in the direction perpendicular to the surface of the drawing sheet of FIG. 5. The line sensor 111 consists of a photodiode array, etc., and is used for detecting the branched light beam 13. The amplifier 121 is used for amplifying the analog output $S_d'$ of the line sensor

111. The A/D converter 122 is used for converting the amplified analog output $S_d'$ to a digital signal and inputting the digital signal to a motor controller 87. The leaky mode measuring apparatus of the fourth embodiment is further differentiated from that of FIG. 3 in that the output $S_s$ of the A/D converter 22 is input only to the motor controller 87 and that the output signal $S_p$ of an encoder 86 is also input to a signal processing section 23.

The line sensor 111 includes a large number of light-receiving elements juxtaposed in the direction (direction of arrow X) where a dark line D occurring in the totally reflected light beam 13 is moved. This line sensor 11 is capable of detecting the dark line D over a wider range than the range in which the movable two-piece photodiode 17 detects the dark line D.

In the fourth embodiment, a second measurement and measurements thereafter are started in the same manner as that in the apparatus of FIG. 3, with the two-piece photodiode 17 disposed at the same position as the position employed at the time of a first measurement. However, in the fourth embodiment, if the dark line D is moved after measurement, the motor controller 87 controls the stepping motor 85, based on the output $S_s$ of the A/D converter 22. The two-piece photodiode 17 is moved so that the dark line D is always aligned with the gap (center position) between the photodiodes 17a and 17b.

When the two-piece photodiode 17 is moved so that it is aligned with the dark line D, the output signal $S_p$ of the encoder 86 corresponds to the amount that the dark line D is moved. Therefore, if the output signal $S_p$ is input to the signal processing section 23 and processed, the refractive index of a sample 11 and the properties of the sample 11 related to the refractive index can be analyzed.

In the case where the movement of the two-piece photodiode 17 is controlled only based on the output $S_s$ of the A/D converter 22, there are cases where the direction of the two-piece photodiode 17 to follow the dark line D cannot be judged, when movement of the dark line D is so great that it is moved away from both the photodiode 17a and the photodiode 17b. The line sensor 111 is provided to avoid the occurrence of such a problem.

That is, the analog output $S_d'$ of the line sensor 111 representing the position of the dark line D is amplified by the amplifier 121 and is input to the A/D converter 122, and the digital output $S_s'$ of the A/D converter 122 is input to the motor controller 87. Based on the digital output $S_s'$ representing the position of the dark line D, the motor controller 87 determines the direction and amount that the stepping motor 85 is driven, and causes the two-piece photodiode 17 to follow the dark line D.

Note that the construction, in which the two-piece photodiode 17 is caused to follow the dark line D and the sample 11 is analyzed based on the position of the two-piece photodiode 17 (i.e., the output signal $S_p$ of the encoder 86), is also applicable to the first, second, and third embodiments described above.

In addition, it is not always necessary to provide the construction in which the direction and quantity that the two-piece photodiode 17 are driven are determined based on the output $S_d'$ of the line sensor 111. However, it is preferable to adapt this construction to cause the two-piece photodiode 17 to follow the dark line D reliably.

Furthermore, a rotary encoder and a linear encoder can be employed as the encoder 86 for detecting the position of the two-piece photodiode 17. The same is true of the aforementioned first, second, and third embodiments.

Finally, while the present invention has been described with reference to the preferred embodiments thereof, the invention is not to be limited to the details given herein, but may be modified within the scope of the invention hereinafter claimed.

What is claimed is:

1. A measuring apparatus utilizing attenuated total reflection, comprising:
    a dielectric block;
    a thin film layer, formed on one surface of said dielectric block, for placing a sample thereon;
    a light source for emitting a light beam;
    an optical system for making said light beam enter said dielectric block at various angles of incidence so that a condition for total internal reflection is satisfied at an interface between said dielectric block and said thin film layer;
    photodetection means, comprising a plurality of light-receiving elements juxtaposed in a predetermined direction and disposed to respectively receive components of said light beam totally reflected at said interface, for detecting attenuated total reflection from a dark line occurring in the totally reflected light beam;
    movement means for moving said photodetection means in the direction where said plurality of light-receiving elements are juxtaposed;
    position detection means for detecting position of said photodetection means moved by said movement means;
    storage means for storing the position of said photodetection means detected by said position detection means; and
    control means for controlling said movement means when said attenuated total reflection is detected a plurality of times for a single sample, by disposing said photodetection means at a predetermined position relative to said dark line when a first measurement is made and also disposing said photodetection means at the same position as said predetermined position stored in said storage means when a second measurement and measurements thereafter are made.

2. The measuring apparatus as set forth in claim 1, wherein said photodetection means comprises a two-piece photodiode.

3. The measuring apparatus as set forth in claim 1, wherein said photodetection means comprises a photodiode array.

4. A measuring apparatus utilizing attenuated total reflection, comprising:
    a dielectric block;
    a metal film, formed on one surface of said dielectric block, for placing a sample thereon;
    a light source for emitting a light beam;
    an optical system for making said light beam enter said dielectric block at various angles of incidence so that a condition for total internal reflection is satisfied at an interface between said dielectric block and said metal film;
    photodetection means, comprising a plurality of light-receiving elements juxtaposed in a predetermined direction and disposed to respectively receive components of said light beam totally reflected at said interface, for detecting attenuated total reflection due to surface plasmon resonance from a dark line occurring in the totally reflected light beam;
    movement means for moving said photodetection means in the direction where said plurality of light-receiving elements are juxtaposed;

position detection means for detecting position of said photodetection means moved by said movement means;

storage means for storing the position of said photodetection means detected by said position detection means; and control means for controlling said movement means when said attenuated total reflection is detected a plurality of times for a single sample, by disposing said photodetection means at a predetermined position relative to said dark line when a first measurement is made and also disposing said photodetection means at the same position as said predetermined position stored in said storage means when a second measurement and measurements thereafter are made.

5. The measuring apparatus as set forth in claim 4, wherein said photodetection means comprises a two-piece photodiode.

6. The measuring apparatus as set forth in claim 4, wherein said photodetection means comprises a photodiode array.

7. A measuring apparatus utilizing attenuated total reflection, comprising:

a dielectric block;

a cladding layer formed on one surface of said dielectric block;

an optical waveguide layer, formed on said cladding layer, for placing a sample thereon;

a light source for emitting a light beam;

an optical system for making said light beam enter said dielectric block at various angles of incidence so that a condition for total internal reflection is satisfied at an interface between said dielectric block and said cladding layer;

photodetection means, comprising a plurality of light-receiving elements juxtaposed in a predetermined direction and disposed to respectively receive components of said light beam totally reflected at said interface, for detecting attenuated total reflection due to a waveguide mode excited in said optical waveguide layer, from a dark line occurring in the totally reflected light beam;

movement means for moving said photodetection means in the direction where said plurality of light-receiving elements are juxtaposed;

position detection means for detecting position of said photodetection means moved by said movement means;

storage means for storing the position of said photodetection means detected by said position detection means; and control means for controlling said movement means when said attenuated total reflection is detected a plurality of times for a single sample, by disposing said photodetection means at a predetermined position relative to said dark line when a first measurement is made and also disposing said photodetection means at the same position as said predetermined position stored in said storage means when a second measurement and measurements thereafter are made.

8. The measuring apparatus as set forth in claim 7, wherein said photodetection means comprises a two-piece photodiode.

9. The measuring apparatus as set forth in claim 7, wherein said photodetection means comprises a photodiode array.

* * * * *